(12) United States Patent
Herrmann et al.

(10) Patent No.: US 11,869,498 B2
(45) Date of Patent: Jan. 9, 2024

(54) SURGICAL SYSTEM CONTROL BASED ON VOICE COMMANDS

(71) Applicant: Stryker European Operations Limited, Carrigtwohill (IE)

(72) Inventors: Florian Herrmann, Schwanau (DE); Fadi Ghanam, Schallstadt (DE)

(73) Assignee: Stryker European Operations Limited, Carrigtwohill (IE)

( * ) Notice: Subject to any disclaimer, the term of this patent is extended or adjusted under 35 U.S.C. 154(b) by 80 days.

(21) Appl. No.: 17/223,586

(22) Filed: Apr. 6, 2021

(65) Prior Publication Data

US 2021/0312918 A1    Oct. 7, 2021

(30) Foreign Application Priority Data

Apr. 7, 2020  (EP) .................................... 20168374

(51) Int. Cl.
*G10L 15/22* (2006.01)
*A61B 17/00* (2006.01)
(Continued)

(52) U.S. Cl.
CPC .............. *G10L 15/22* (2013.01); *A61B 17/00* (2013.01); *G10L 21/0208* (2013.01); *H04R 1/08* (2013.01);
(Continued)

(58) Field of Classification Search
CPC ..... G10L 15/22; G10L 15/20; G10L 21/0208; G10L 2015/223; G10L 2021/02166; G10L 2021/0216; G10L 21/0216; A61B 17/00; A61B 2017/00203; A61B 2017/00115; A61B 2017/00725; A61B 90/39; A61B 90/00; A61B 2034/2051;
(Continued)

(56) References Cited

U.S. PATENT DOCUMENTS 6,814,490 B1   11/2004  Suhm et al.
9,066,755 B1    6/2015  Jacobs et al.
(Continued)

FOREIGN PATENT DOCUMENTS

| WO | 97015240 A1 | 5/1997 |
| WO | 0150959 A1 | 7/2001 |
| WO | WO2017066373 A1 | 4/2017 |

OTHER PUBLICATIONS

English language abstract for WO 01/50959 A1 extracted from espacenet.com database on Apr. 8, 2021, 2 pages.

*Primary Examiner* — Leshui Zhang
(74) *Attorney, Agent, or Firm* — Howard & Howard Attorneys PLLC

(57) ABSTRACT

A controller for a surgical navigation system is presented. The controller is configured to receive a position signal from a tracking system, wherein the position signal is indicative of a position of a hand-held surgical device that is tracked by the surgical navigation system inside an operation environment. The controller is further configured to receive sound signals from a plurality of microphones directed toward the operation environment, wherein the sound signals potentially contain one or more voice commands from one or more voice sources inside the operation environment. The controller is configured to process the sound signals dependent on the position signal.

12 Claims, 11 Drawing Sheets

(51) Int. Cl.
*G10L 21/0208* (2013.01)
*A61B 34/20* (2016.01)
*H04R 3/00* (2006.01)
*G10L 21/0216* (2013.01)
*H04R 1/08* (2006.01)

(52) U.S. Cl.
CPC ............... *A61B 2017/00203* (2013.01); *G10L 2015/223* (2013.01)

(58) Field of Classification Search
CPC .... A61B 2034/2055; A61B 2034/2063; A61B 34/10; A61B 34/20; A61B 34/30; A61B 2090/3983; A61B 2090/3995; G16H 20/40; G16H 40/40; H04R 1/08; H04R 1/406; H04R 3/00; H04R 3/005; G06F 3/167
USPC ....... 704/275, 272, 226, 233, 237, 238, 246, 704/270; 381/71.1–71.14, 73.1, 92, 93, 381/94.1–94.9, 95, 97, 98–115
See application file for complete search history.

(56) References Cited

U.S. PATENT DOCUMENTS

| | | | |
|---|---|---|---|
| 10,028,794 | B2 | 7/2018 | Cagle et al. |
| 2006/0104454 | A1* | 5/2006 | Guitarte Perez ........ G06F 3/167 704/E21.002 |
| 2006/0281989 | A1 | 12/2006 | Viswanathan et al. |
| 2008/0253589 | A1* | 10/2008 | Trahms ............... G01S 7/52084 704/E15.045 |
| 2009/0141908 | A1* | 6/2009 | Jeong ........................ G01S 5/20 381/92 |
| 2015/0164606 | A1 | 6/2015 | Jacobs et al. |
| 2016/0125882 | A1 | 5/2016 | Contolini et al. |
| 2017/0312035 | A1* | 11/2017 | May ....................... A61B 90/90 |
| 2018/0092706 | A1* | 4/2018 | Anderson .............. A61B 90/50 |
| 2018/0262743 | A1 | 9/2018 | Casas |
| 2018/0262849 | A1* | 9/2018 | Farmani ............... H04R 25/407 |
| 2020/0058284 | A1* | 2/2020 | Miller ................... A61B 46/10 |

* cited by examiner

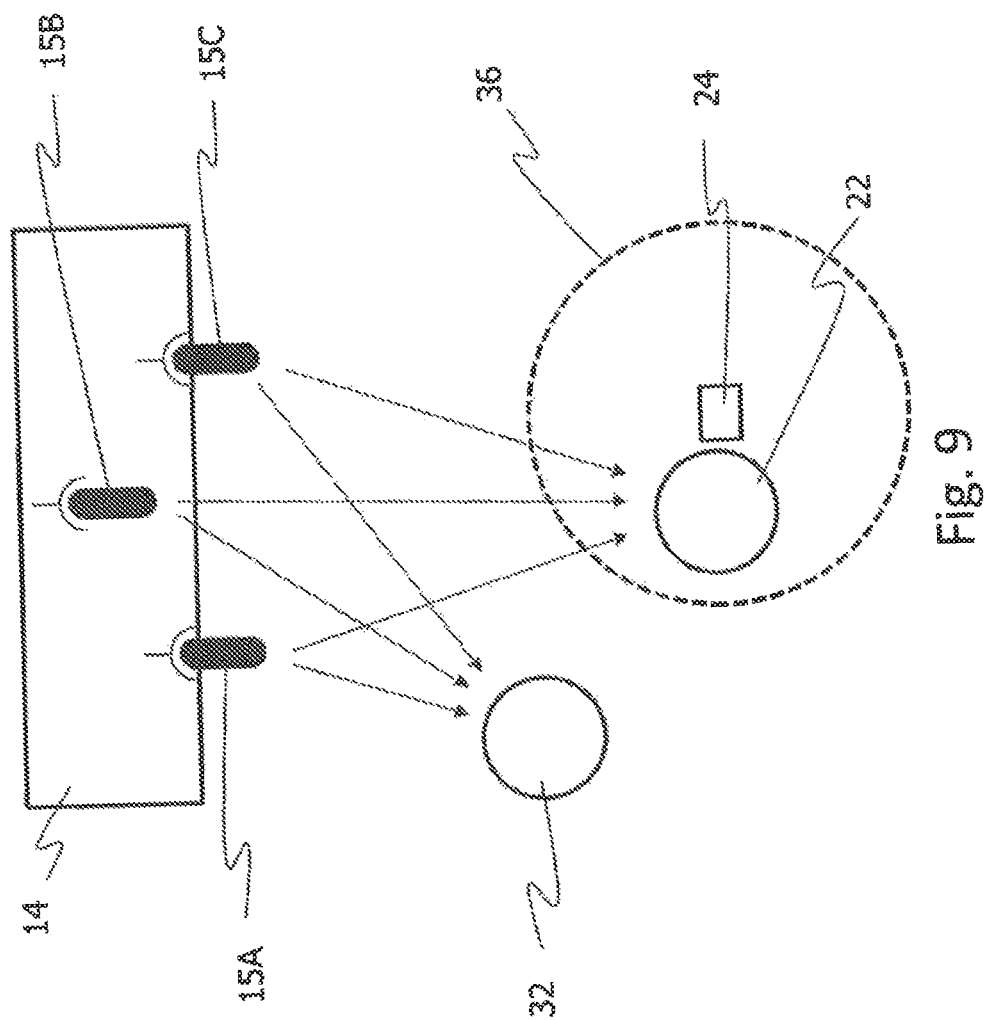

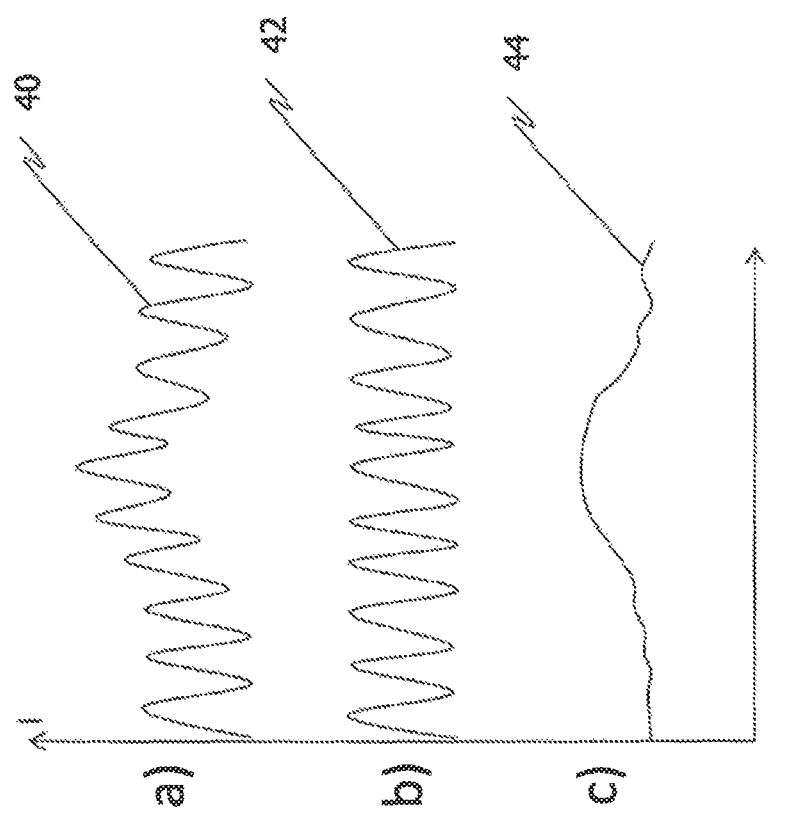

SURGICAL SYSTEM CONTROL BASED ON VOICE COMMANDS

PRIORITY CLAIM

This application claims priority under 35 U.S.C. § 119 to European Patent Application No. 20168374.5, filed Apr. 7, 2020, the entire contents of which are hereby incorporated by reference.

TECHNICAL FIELD

The present disclosure generally relates to surgical assistance techniques. In particular, a controller, a controller system, a surgical system, a method, and a computer program product for processing sound signals from an operation environment are presented. The sound signals potentially contain one or more voice commands from one or more voice sources inside the operation environment.

BACKGROUND

In surgical procedures, the surgeon is regularly assisted by various surgical systems, such as powered surgical instruments, robotic arms, displays, and computers. The surgeon's ability to interact with such an assisting system using a manually-operated input device such as a button, a keyboard or a mouse is limited due to various constraints, such as having to remain sterile or when holding a surgical device.

An alternative way to operate the assisting systems is by issuing voice commands that are received by a microphone. In this regard, U.S. Pat. No. 10,028,794 B2 describes the use of voice commands to control one or more surgical instruments In an operation environment, voice commands may be rendered intelligible by additional sound sources like powered instruments or other surgery personnel. The other surgery personnel may even issue an utterance not intended for operating the assisting surgical system, which may be erroneously interpreted as being a voice commend issued by the surgeon. Such an erroneous interpretation may cause a faulty operation of the assisting surgical system. This can lead to minor problems, such as commands having to be repeated or enunciated slower, but also to major problems, such as assisting surgical system executing wrong commands, which may cause injuries to the patient.

SUMMARY

There is a need for a technique for a voice-controlled operation of a surgical system that solves one or more of the aforementioned or other problems.

According to a first aspect, a controller for a surgical system is provided. The controller is configured to receive a position signal from a tracking system, wherein the position signal is indicative of a position of a hand-held surgical device that is tracked by the tracking system inside an operation environment. The controller is further configured to receive sound signals from a plurality of microphones directed toward the operation environment, wherein the sound signals potentially contain one or more voice commands from one or more voice sources inside the operation environment. The controller is also configured to process the sound signals dependent on the position signal.

The tracking system may be an optical tracking system, an electromagnetic tracking system or any other tracking system suitable for surgical tracking (e.g., in the context of surgical navigation).

The surgical system controlled by the controller may be the tracked hand-held surgical device, a surgical navigation system (including, e.g., the tracking system), or any other system capable of providing surgical assistance.

The controller may be configured to shift the sound signals relative to each other in time. This shifting may be performed based on the position signal. The controller may further be configured to then superpose the shifted sound signals to generate a superposition signal in such a way that sound signals received from a focus position related to the position of the hand-held surgical device interfere constructively.

The focus position may have a predetermined spatial relationship with the position of the tracked hand-held surgical device. The predetermined spatial relationship may depend on at least one of an orientation of the tracked hand-held surgical device, an operating mode of the hand-held surgical device, and profile data associated with the operator. The predetermined spatial relationship may be described by a vector in space between the focus position and the position of the tracked hand-held surgical device, including the zero or null vector. The predetermined relationship may generally be defined to extend from the position of the tracked hand-held surgical device to the estimated position of the head of a person operating the hand-held surgical device.

The controller may be configured to determine that there exists a voice command originating from an operator of the hand-held surgical device if the superposition signal contains a voice command that satisfies at least one detection condition. The at least one detection condition may be based on a threshold. For example, the at least one condition may be based on a threshold for at least one of an intensity and a signal-to-noise ratio.

The controller may be configured to determine, based on sound signals received from the plurality of microphones, a position of a voice source of a voice command included in each of the sound signals. The controller may further be configured to determine that the voice command originates from an operator of the hand-held surgical device based on a comparison condition that evaluates a relationship between the determined position of the voice source and the position signal from the tracking system. The comparison condition may take into account at least one of a determined orientation of the tracked hand-held surgical device, an operating mode of the hand-held surgical device, and profile data associated with the operator.

The controller may be configured to determine for each of the sound signals a trigger moment, in which an intensity of a sound signal exceeds a predetermined trigger threshold. The controller may further be configured to determine the position of the voice source based on a time relationship between the trigger moments. Alternatively, or in addition, the controller may be configured to shift the sound signals relative to each other in time so as to temporally align the sound signals with respect to the voice command included in each sound signal and determine the position of the voice source based on the time shifts for the temporal alignment of the sound signals.

The controller may be configured to generate a cancellation signal for at least one sound signal, wherein the cancellation signal is indicative of an interference signal contained in the sound signal. Moreover, the controller may be configured to at least partially cancel the interfering signal from the at least one sound signal using the cancellation signal. The controller may further be configured to generate the cancellation signal taking into account at least one parameter selected from a parameter set comprising a type of hand-held device and one or more operating parameters of the hand-held device. The cancellation signal may comprise a pre-recorded sound signal.

According to a second aspect, a controller system provided. The controller system comprises a controller as described herein and a calibration device comprising a tracker trackable by the tracking system and a speaker configured to emit sound detectable by the plurality of microphones.

The calibration device may comprise the hand-held surgical device. In some variants, the hand-held surgical tool is properly equipped to constitute the calibration device.

The tracking system may be associated with a first coordinate system, the plurality of microphones may be associated with a second coordinate system. The controller may have access to a first spatial relationship of the tracker relative to the speaker. The tracking system may be configured to determine a second spatial relationship of the tracker relative to the first coordinate system and to determine a third spatial relationship of the speaker relative to the second coordinate system. The tracking system may further be configured to determine a fourth spatial relationship of the first coordinate system relative to the second coordinate system based on the first, second and third spatial relationships.

The controller system may further be configured to determine the second and third spatial relationships for a plurality of positions of the calibration device. The controller may be configured to determine the fourth spatial relationship of the first coordinate system relative to the second coordinate system based on the plurality of determined second and third spatial relationships. The controller may be configured to continuously determine a plurality of fourth spatial relationships of the first coordinate system relative to the second coordinate system based on the plurality of determined second and third spatial relationships, while the operator is moving the calibration device.

According to a third aspect, a surgical system is provided. The surgical system comprises a controller or a controller system as described herein, the tracking system, and the plurality of microphones.

According to a fourth aspect, a method for operating a surgical system is provided. The method comprises receiving a position signal from a tracking system, wherein the position signal is indicative of a position of a hand-held surgical device that is tracked by the tracking system inside an operation environment. The method further comprises receiving a sound signal from a plurality of microphones directed towards the operation environment, wherein the sound signals potentially contain one or more voice commands received from one or more voice sources inside the operation environment. The method also comprises processing the sound signals dependent on the position signal.

According to a fifth aspect, a computer program product is provided. The computer program product comprises instructions that, when executed on at least one processor, cause the at least one processor to carry out the method described herein.

The computer program product may be stored on a computer readable medium. The computer program product may be stored on a non-transitory computer readable medium.

BRIEF DESCRIPTION OF THE DRAWINGS

Further details, advantages and aspects of the present disclosure will become apparent from the following embodiments taken in conjunction with the drawings, wherein:

FIG. 9 shows an operator and a non-operator issuing commands, wherein a proximity threshold around the surgical device is used to validate the issued voice commands from the operator;

FIG. 12 shows sound signals involved in cancelling an interference signal in a sound signal from a microphone;

DETAILED DESCRIPTION

Figure 1:
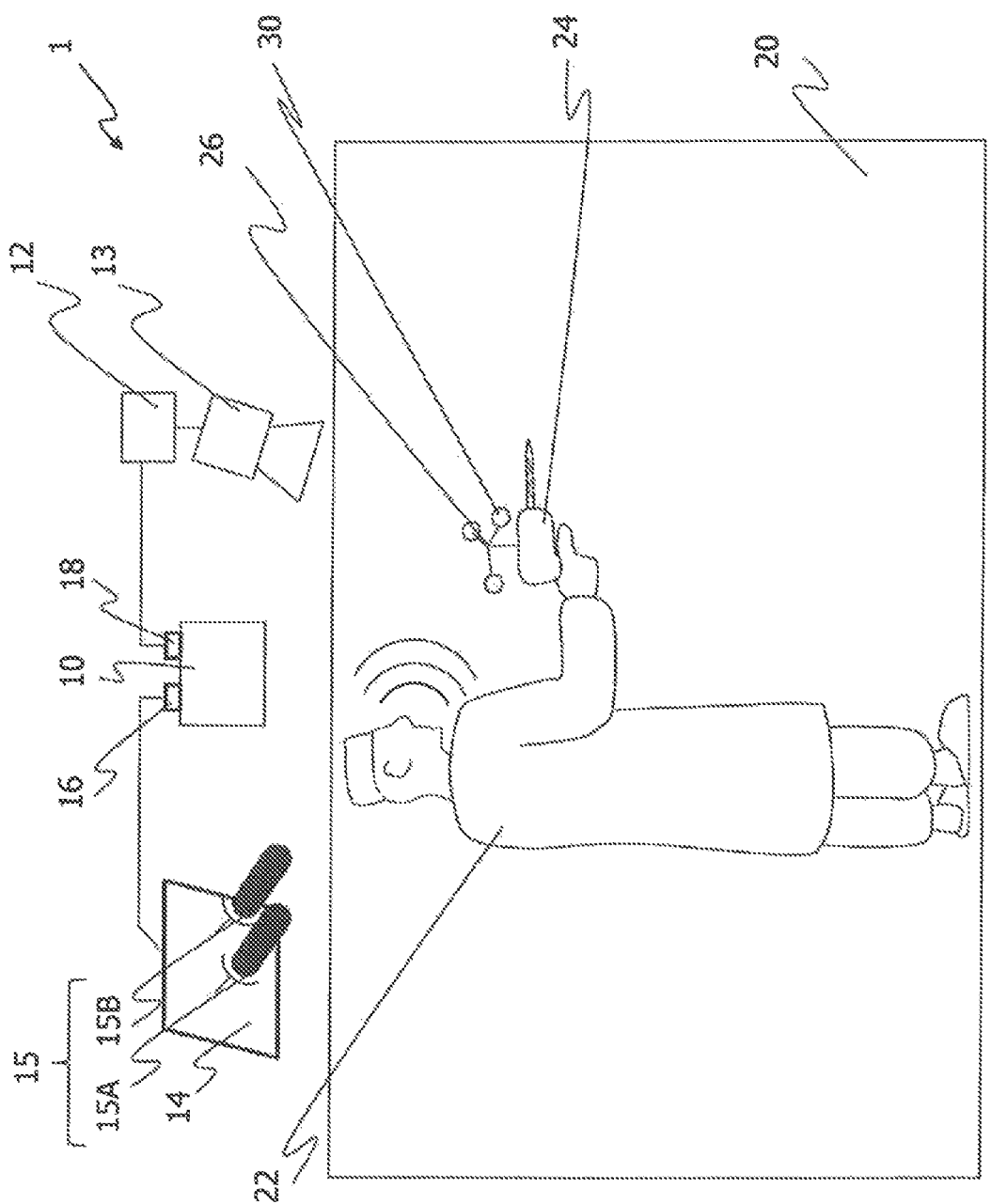
FIG. 1 shows a first embodiment of a surgical system controllable by voice commands.

In the following description of exemplary embodiments, the same reference numerals are used to denote the same or similar components.

FIG. 1 shows a surgical system 1 comprising a controller 10, a tracking system 12 and a microphone array 14 comprising a plurality of microphones 15 (e.g., two microphones 15A, 15b). The tracking system 12 shown in FIG. 1 is an optical tracking system 12. However, any other tracking technology suitable for surgical tracking (e.g., an electromagnetic tracking system) may be used.

The controller 10 may comprise or consist of at least one of a computer chip, expansion card, a stand-alone device, and circuitry that allows signal processing. As such, the controller 10 may be realized by a computer, cloud computing resources, or a network of computers. The controller 10 may also be realized by a controller that is operating a different entity, such as the tracking system 12, the microphone array 14, a surgical navigation system (that may include the tracking system 12), a computer managing patient data (e.g., displaying patient image data in real time during a surgical operation), and so on.

The controller 10 is configured to receive a position signal from the tracking system 12 and to receive sound signals from the plurality of microphones 15. To this end, the controller 10 comprises interfaces 16, 18 over which the controller 10 can receive the position signal and the sound signals, respectively. The interfaces 16, 18 shown in FIG. 1 comprise electrical lines. However, the interfaces 16, 18 may also comprise at least one air interface. The controller 10 may be configured for only receiving data via the interfaces 16, 18. Alternatively, the controller 10 may be configured to receive and send data, for example so that the controller 10 can send control signals to the tracking system 12 and/or the microphone array 14.

The tracking system 12 comprises a camera 13 that is configured to receive light from a surgical operation environment 20. The camera 13 may be configured to receive light in a selected light spectrum, such as infrared light, visible light, or ultraviolet light. The camera 13 is configured to generate image data based on the light received from the operation environment 20. In some variants, the camera 13 is realized as a stereo camera so as to generate three-dimensional image data The tracking system 12 is configured to determine a position of a trackable object, also called tracker herein, based on the image data. Additionally, the tracking system 12 may be configured to determine an orientation of the trackable object. Determining the object position may comprise having access to geometric properties of the trackable object. The trackable object may comprise markings or tracking elements that reflect and/or emit light and that have a predetermined geometric relationship to each other. Based on a size and shape of the trackable object determined in the image data and the known geometric properties, the tracking system 12 may determine the position and/or orientation of the trackable object.

FIG. 1 shows an operator 22, such as a surgeon, holding a hand-held surgical device 24. Attached to the surgical device 24 is a trackable object in the form of a device tracker 26 trackable by the tracking system 12. The device tracker 26 shown in FIG. 1 comprises three optical tracking elements 30. The optical tracking elements 30 may, for example, emit light or reflect light emitted by a light source (not shown) of the tracking system 12. The light may be visible light or infrared light.

The tracking elements 30 are arranged in a geometric configuration relative to the surgical device 24 that is known to the tracking system 12. Based on images of the tracker device 26 and the known geometric configuration, the tracking system 12 can determine a position and orientation of the device tracker 26 and the surgical device 24.

The device tracker 26 may comprise any other type, number and configuration of tracking elements. For example, in the case of an electromagnetic tracking system, the tracker may comprise one or more coils as tracking elements. The electromagnetic tracking system may further comprise a field generator generating a magnetic field detectable by the one or more coils as well as a locator electrically connected with the one or more coils and configured for determining at least one of an orientation and a position of the tracker (and, thus, to track the surgical device 24).

The device tracker 26 may be an integral part of the surgical device 24 or detachably attached to the surgical device 24. The surgical device 24 does not even require a dedicated device tracker 26 in order to be trackable by the tracking system 12. Rather, the tracking system 12 may be configured to track the surgical device 24 itself, for example based on a shape, markings or colouring of the surgical device 24.

The microphone array 14 shown in FIG. 1 comprises two microphones 15A, 15B. As will be described in more detail below, the microphone array 14 may comprise more than two microphones. The two microphones 15A, 15B are directed towards the operation environment 20 and can therefore (at least) receive sound emitted from sound sources in the operation environment 20. The two microphones 15A, 15B are arranged spatially in a spaced-apart configuration. Therefore, a sound source located in the operation environment 20 has a first distance to the first microphone 15A and a typically different second distance to the second microphone 15B. Sound emitted by the sound source has to travel the first distance to the first microphone 15A and the second distance to the second microphone, which results in a first and a second travel time. Due to different travel times, sound signals received at the two microphones 15A, 15B may be temporally offset relative to each other. As will be described later below, these temporal offsets can be used or modified when processing the sound signals for validation or control purposes.

Figure 2:
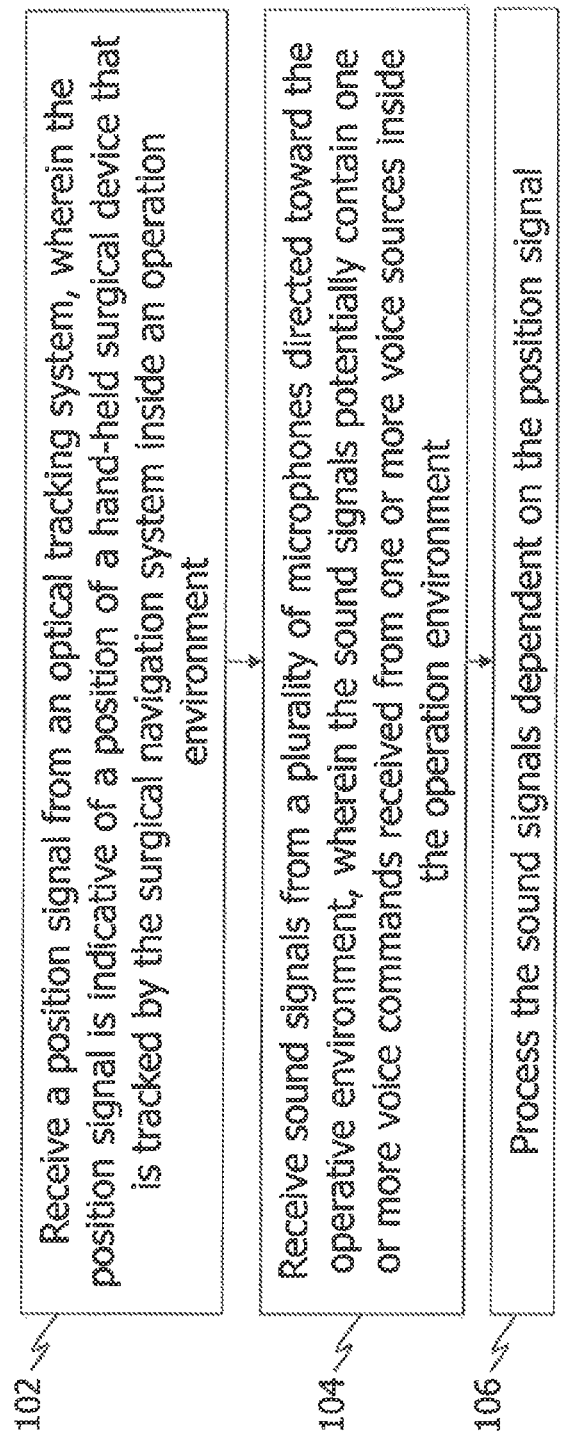
FIG. 2 shows a flow diagram for a method for operating a surgical system.

FIG. 2 shows a flow diagram 100 for a method for operating a surgical system such as the hand-held surgical device 24, a surgical navigation or imaging system, and so on. It will in the following be assumed that it is the controller 10 of FIG. 1 that performs the method aspects described herein. To this end, the controller 10 may comprise a processor and a non-transitory computer-readable medium storing a computer program product. The computer program product may comprise instructions that, when executed on the processor, cause the processor to carry out any of the method aspects described herein.

The method illustrated in FIG. 2 comprises receiving, in step 102, a position signal from the tracking system 12. The position signal is indicative of a position of the hand-held surgical device 24 that is tracked by the tracking system 12 inside the operation environment 20. The position signal may also be indicative of an orientation of the hand held surgical device 24.

The method further comprises receiving, in step 104, sound signals from the plurality of microphones 15 directed toward the operation environment 20. As will be appreciated, the sound signals potentially contain one or more voice commands from one or more voice sources inside the operation environment 20, including the operator 22 and other surgical personnel. The controller 10 may be configured to receive the sound signals continuously. Alternatively, the controller 10 may be configured to receive the sound signals once a trigger is activated. The trigger may be a sound intensity threshold for at least one of the sound signals, or a manually activated trigger, such as the operator 22 starting to operate the surgical device 24.

The method also comprises processing, in step 106, the sound signals dependent on the position signal. Step 106 of processing the sound signals dependent on the position signal may comprise various approaches. According to a first approach, the controller 10 is essentially configured to validate, or verify, an issued command by comparing locations determined from sound signals and the tracking system 12. According to a second approach, the controller 10 is essentially configured to perform beamforming towards one of the surgical device 24 and its operator 22. Of course, step 106 of processing the sound signals dependent on the position signal may comprise still further approaches not described in more detail herein.

According to the first approach, step 106 of processing the sound signals dependent on the position signal comprises determining, based on sound signals received from the plurality of microphones 15, a position of a voice command included in each of the sound signals. It may then further determined, or validated, that the voice command actually originates from the operator 22 of the hand-held surgical device 24 based on a comparison condition that evaluates a relationship between the determined position of the voice command and the position signal from the tracking system 12.

Determining the position of the voice command included in each of the sound signals may be based on different durations for a time of flight of sound that is the result of the microphones 15 being arranged spaced apart.

Figure 3:
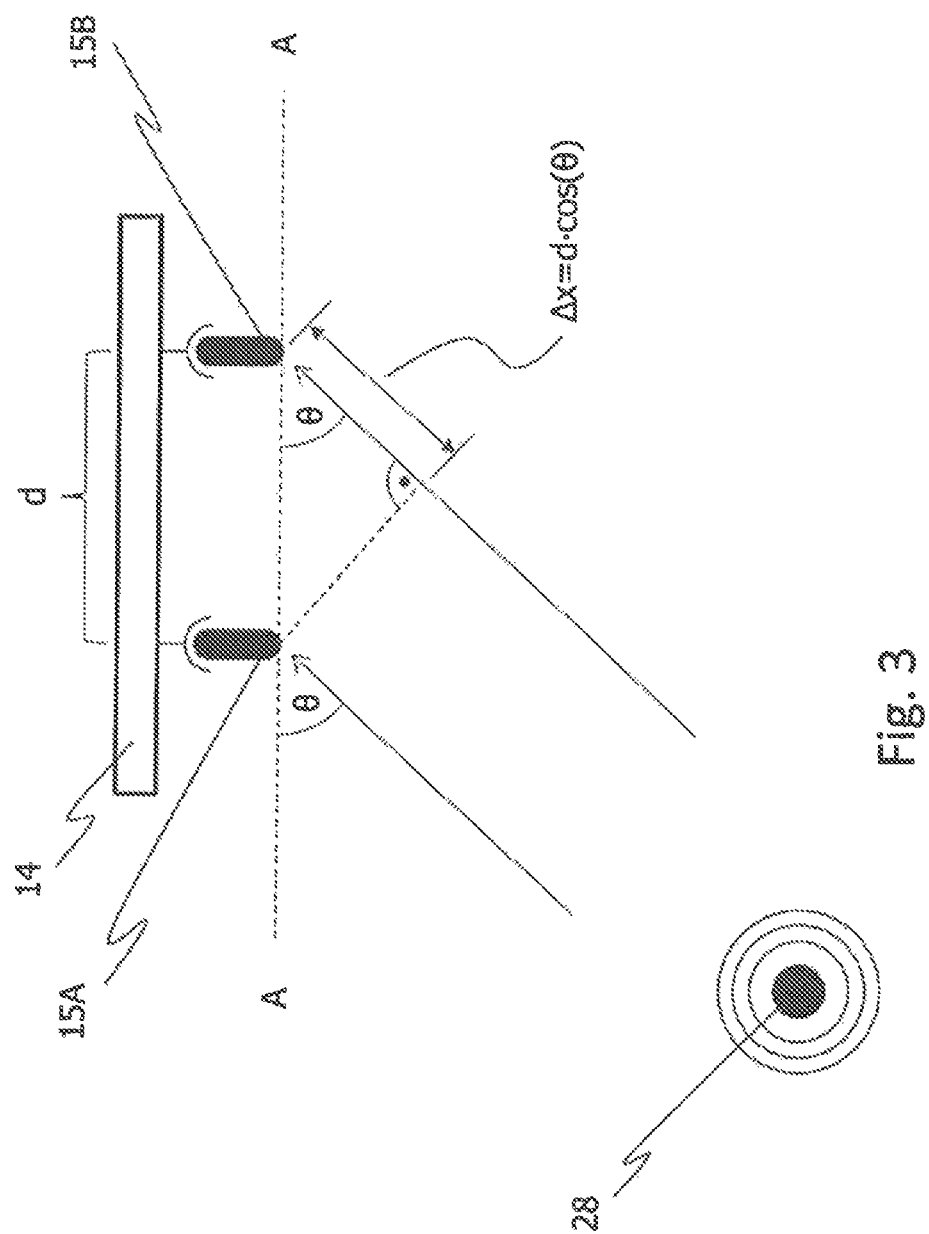
FIG. 3 shows a diagram for an approximation of travel paths of sound emitted from a sound source received at two microphones.

FIG. 3 shows a diagram for an approximation of travel paths of sound emitted from a sound source 28, such as the operator 22 or another person in the operation environment 20, and received at the two microphones 15A, 15B. In this approximation it is assumed that the sound emitted from the sound source 28 arrives at both microphones 15A, 15B at the same incident angle θ (tetha). This approximation is particularly justified for a small distance d between both microphones 15A, 15B and a large distance between the sound source 28 and the microphone array 14. Under this assumption, a path difference Δx between the distances from the sound source to the different microphones 15A, 15B may be determined using the formula $$\Delta x = d \cdot \cos(\theta).$$ equation (1)

With the velocity of sound in air $v_{sound}$, a time offset $\Delta t$ between sound arriving at microphone 15A and arriving at microphone 15B can be calculated using the formula $$\Delta t = \frac{d \cdot \cos(\theta)}{v_{sound}}$$ equation (2)

Therefore, based on a determined time offset Δt for sound received at the two microphones 15A, 15B, the incident angle θ can be determined from:

$$\theta = \arccos\left(\frac{\Delta t \cdot v_{sound}}{d}\right).$$ equation (3)

Due to the rotational symmetry of the microphone array 14 around an axis A-A through both microphones 15A, 15B, the direction of the sound source is described by a cone around the axis A-A with an opening angle of the incident angle θ. It is noted, that the shape of a cone is a result of the approximation described above. A more accurate calculation that takes into account a finite distance between the sound source 28 and the microphones 15A, 15B would result in a hyperboloid.

One way to eliminate the ambiguity that results from the rotational symmetry is to define a plane that intersects the cone. Such a plane may be a horizontal plane at a height of an average adult human being, i.e., a height at which voice commands are issued. In this case, the microphone array 14 may be arranged at the height of the average human being (or customized to the height of the operator 22), wherein the axis A-A through both microphones 15A, 15B is oriented horizontally. Since in such a case a voice command issued by, for example, the operator 22 travels to the microphones 15A, 15B in an essentially horizontal line, the direction of the voice command can be unambiguously determined based on the incident angle θ obtained by equation (3).

As can be seen from the above, only a direction towards the sound source 28, but not a position of the sound source 28 in space can be determined from equation (3). A position of the sound source 28 can be determined by using three or more microphones 15 that are arranged in a plane (and not in a line). When using three microphones 15A, 15B, 15C (see, e.g., in FIG. 4), the above calculation can be performed for three pairs of microphones, i.e., 15A and 15B, 15B and 15C, and 15A and 15C. These calculations result in three cones (or more precisely: three hyperboloids), which intersect in a point in space that is the location of the sound source 28. The accuracy of the calculation can be improved by using more than three microphones. Each additional microphone increases the number of cones or hyperboloids that can be calculated. The location of the sound source 28 may be determined as an average or weighted average of intersections of at least some of the determined cones or hyperboloids.

As described above, the direction or even the position of the sound source 28 can be determined using time offsets between sound signals of different microphones 15. These time offsets can be determined using different techniques, which will be described using the (non-limiting) example of a microphone array 14 shown in FIG. 4.

Figure 4:
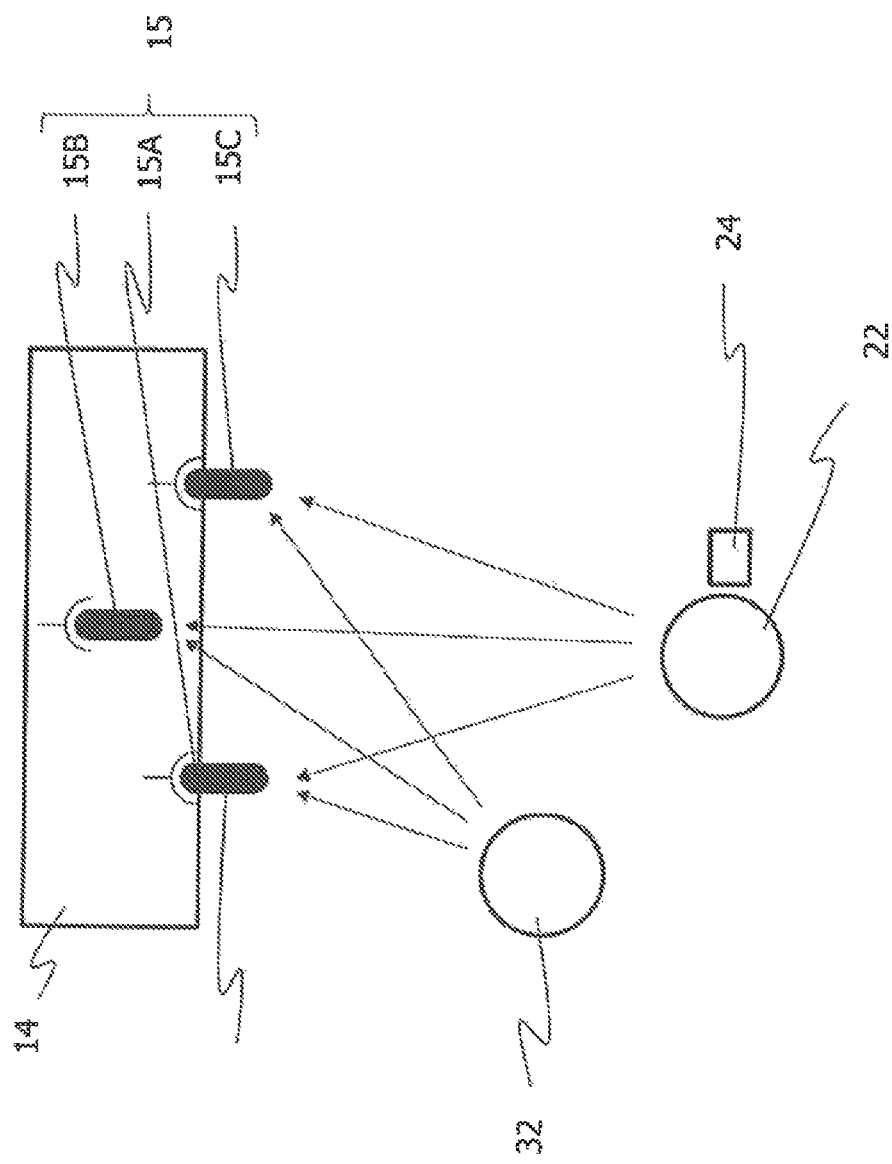
FIG. 4 shows an example of a microphone array comprising three microphones.

The microphone array 14 of FIG. 4 comprises three microphones 15A, 15B, 15C, each of which generates a sound signal indicative of received sound. As explained above, any other number of microphones larger than one can be used. The microphones 15A, 15B, 15C are generally directed towards the operator 22 holding the surgical device 24 and non-operator 32, who is not holding the surgical device 24. As indicated by the arrows in FIG. 4, sound emitted by the operator 22 and the non-operator 32 travels a different distance resulting in different time spans required in order for sound to reach each of the microphones 15A, 15B, 15C.

Figure 5:
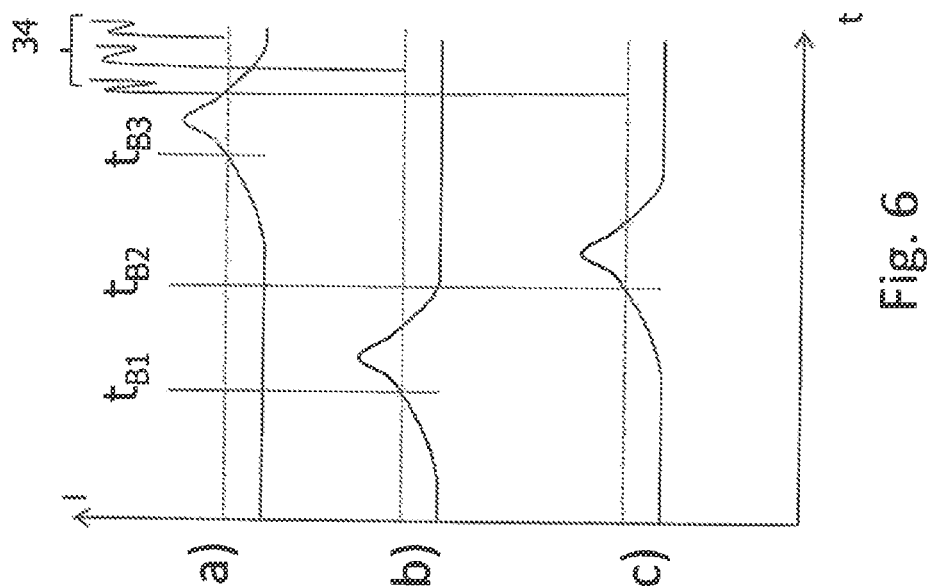
FIG. 5 shows sound signals caused by a voice command issued by a non-operator of a tracked handheld surgical device.
Figure 6:
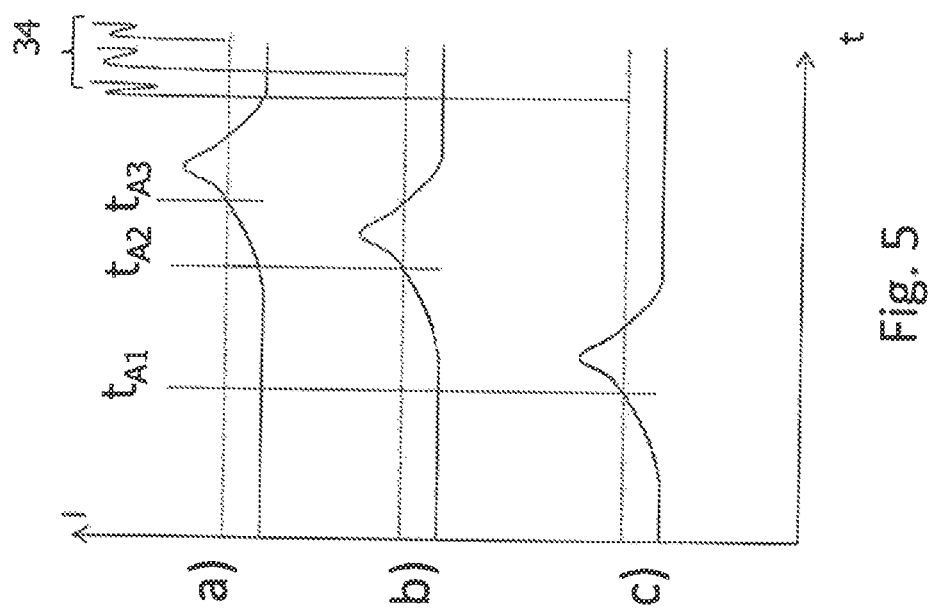
FIG. 6 shows sound signals caused by a voice command issued by an operator of a tracked handheld surgical device.

Examples of sound signals generated by the microphones 15A, 15B, 15C are shown in FIGS. 5 and 6, wherein FIG. 5 shows sound signals caused by a voice command issued by the non-operator 32 and FIG. 6 shows sound signals caused by a voice command issued by the operator 22. The sound signals a), b), and c) are generated by the microphones 15A, 15B, 15C, respectively. As can be seen in FIGS. 5 and 6, the sound signals for each voice command are shifted in time relative to each other, due to the spatial distance between the microphones 15A, 15B, 15C. Furthermore, the shift of the sound signals differs for the operator 22 and the non-operator 32, due to their different spatial relationship relative to the microphones 15A, 15B, 15C.

One technique for determining the temporal offset between the sound signals is to define a predetermined trigger threshold. The trigger threshold can comprise at least one of a threshold for a sound intensity and a threshold for a signal-to-noise-ratio. FIGS. 5 and 6 show a predetermined trigger threshold 34 for the sound intensity. A point in time in a sound signal is marked as a trigger moment $t_{A1}$, $t_{A2}$, $t_{A3}$, $t_{B1}$, $t_{B2}$, $t_{B3}$ when a sound signal exceeds the trigger threshold. The time offsets between sound signals can be calculated from time differences between the trigger moments $t_{A1}$, $t_{A2}$, $t_{A3}$, $t_{B1}$, $t_{B2}$, $t_{B3}$. Determining time offsets using trigger moments requires little processing and is therefore resource-efficient.

Figure 8:
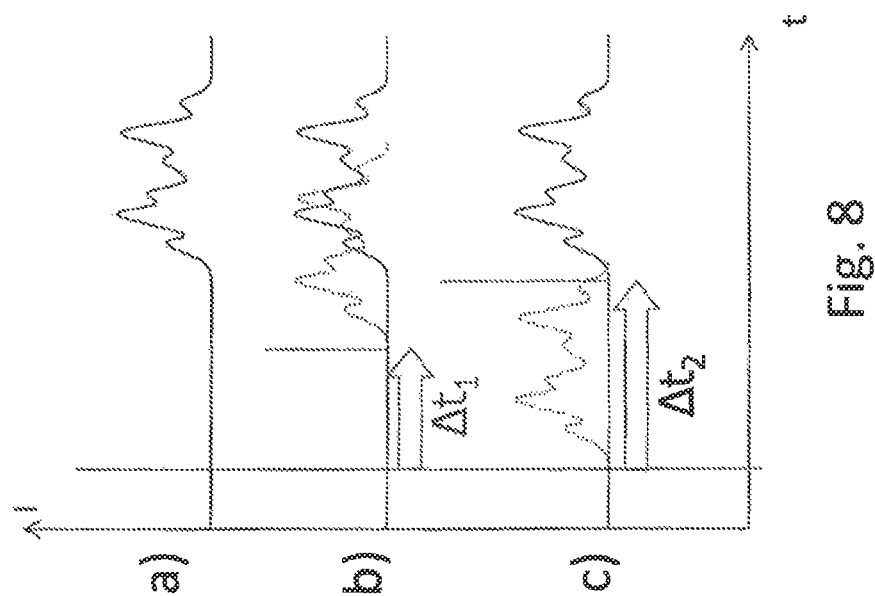
FIG. 8 shows the sound signals of FIG. 7 after being shifted relative to each other.
Figure 7:
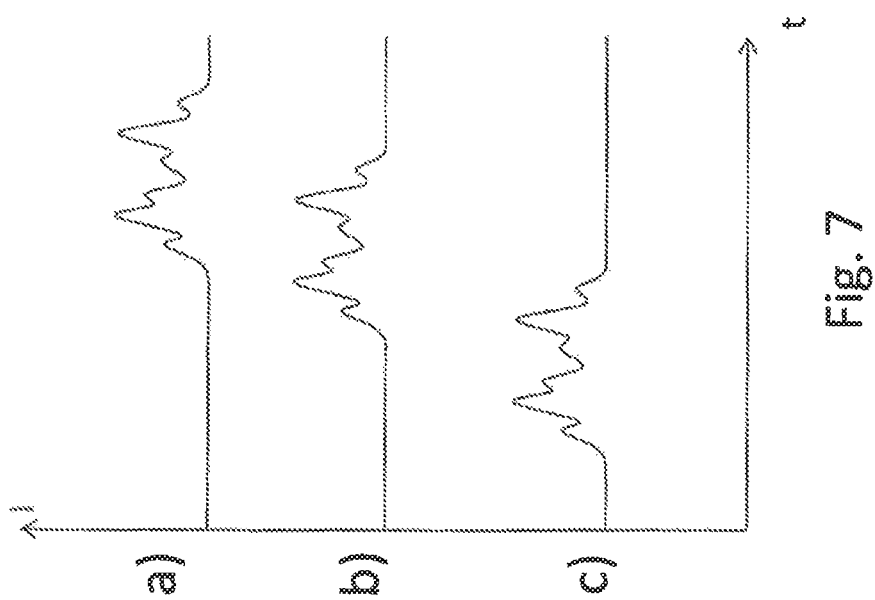
FIG. 7 shows sound signals of a voice command received at three microphones.

Another technique for determining the temporal offsets is to shift the sound signals relative to each other in time so as to temporally align the sound signals with respect to the voice command included in each sound signal. FIGS. 7 and 8 show a voice command (e.g., issued by the operator 22) received at the microphones 15A, 15B, 15C. FIG. 7 shows the sound signals as received and FIG. 8 shows the sound signals after being shifted.

As can be seen in FIG. 7, despite the temporal offset of the sound signals, the shape of the sound signals is similar, because they are caused by the same voice command. The controller 10 may be configured to identify the similar shape of the sound signals that need to be aligned. The identification may comprise applying a Fourier analysis to the sound signals.

FIG. 8 shows the sound signals of the microphones 15B (label b)) and 15C (label c)) aligned with the sound signal of the microphone 15A (label a)). The time offset required for the alignment is the time offset that can be used for determining the position of the voice command.

As explained above, the controller 10 may determine the position of a source of the voice command by using trigger moments or by aligning the sound signals. Moreover, as defined in step 102, the controller is configured to receive a position signal from a tracking system 12, wherein the position signal is indicative of a position of the hand-held surgical device 24. Therefore, the controller 10 receives information about two positions: the position of the source of the voice command and the position indicative of the hand-held surgical device 24.

Based on this information, the controller 10 may determine that the voice command originates from the operator 22 of the hand-held surgical device 24 based on a comparison condition that evaluates a relationship between the determined position of the source of the voice command and the position signal from the tracking system 12.

The comparison condition may comprise defining a proximity threshold around the surgical device 24 or the operator 22. FIG. 9 shows an operator 22 and a non-operator 32 issuing commands, wherein a proximity threshold around the surgical device 24 is used to validate the issued voice commands. When the operator 22 (as an exemplary voice source) issues a voice command, the controller 10 is configured to determine the position of the voice source of that voice command based on the sound signals received from the microphones 15A, 15B, 15C. The determination may be performed by any of the two techniques described above. The controller 10 is also configured to determine a distance between the position of the voice source and the position of the surgical device 24. The controller 10 may define or have access to a predetermined distance 36. The predetermined distance 36 in the present example may be 1 m. Alternatively, the predetermined distance 36 may be larger (e.g., 2 m) or smaller (e.g., 50 cm).

In the case that the determined distance is smaller than the predetermined distance 36 (e.g., smaller than 1 m), the controller 10 determines that the voice command was issued by the operator 22 as voice source. The controller 10 may consequently positively validate the voice command and forward the voice command, or a control signal derived therefrom, to the surgical system 1 the command was intended for, such as the surgical device 24.

When the non-operator 32, as another exemplary voice source, issues a voice command, the controller 10 determines that a distance between the position of that voice source and the position of the surgical device 24 exceeds the predetermined distance 36 (e.g., smaller than 1 m). Consequently, the command may be dismissed as a voice command not issued by the operator 22. As a consequence, voice-controlled operation of a surgical system 1 as a result of an utterance of the non-operator 32 is avoided, and the safety and efficiency of the surgical procedure are improved.

The comparison condition is of course not limited to a proximity threshold. The comparison condition may take into account at least one of a determined orientation of the surgical device 24, an operating mode of the surgical device 24, and profile data associated with the operator 22. The profile data may include the height or a individual setting of the operator 22.

The comparison condition does not necessarily have to relate to the position of the surgical device 24. The surgical device 24 is held in the hand of the operator 22 and therefore spaced apart from the location of the voice command, namely the head (i.e., mouth) of the operator 22. The comparison condition may take this into account by adding a spatial offset (e.g., a vector) to the position of the surgical device 24 that translates the position of the surgical device 24, for example by 50 cm, towards the mouth of the operator 22. The added offset may also depend on at least one of an orientation of the surgical device 24 and whether the surgical device 24 is being operated. The spatial offset increases the accuracy for determining whether the voice command originates from an operator 22 of the hand-held surgical device 24.

The above described approach is one way to process sound signals dependent on the position signals, as defined by step 106 of the method illustrated in FIG. 2. Another way of processing sound signals dependent on the position signal is to perform beamforming.

A common way to perform beamforming is to shift sound signals received at the plurality of microphones 15A, 15B, 15C relative to each other in time and then superposing the shifted sound signals to generate a superposition signal in such a way that sound signals receive from a sound source interfere constructively.

Generally, in order to properly perform beamforming, the position of the sound source needs to be known. Based on the position of the sound source, a direction from the microphone array 14 towards the sound source may be calculated in form of incident angles. These incident angles allow calculating time offsets that have to be applied to each of the microphones (e.g., based on equation (2)). Once the sound signals of each microphone 15 have been shifted, the sound signals can be superposed. The resulting superimposed sound signal interferes constructively for sound emitted by the sound source.

The principle of beamforming may be applied to the controller 10 of FIG. 1 as follows. The controller 10 may be configured to shift, based on the position signal from the tracking system 12, the sound signals relative to each other in time and then superpose the shifted sound signals to generate a superposition signal in such a way that sound signals received from a focus position related to (e.g., corresponding to or shifted relative to) the position of the hand-held surgical device 24 interfere constructively. The focus position may be the position of the surgical device 24 itself. Since the operator 22 who issues a command is also the person holding the surgical device 24, focusing the reception of the microphone array 14 towards the surgical device 24 improves the signal quality of the operator's 22 voice command in the superimposed sound signal.

The quality can be further improved by defining a focus position that has a predetermined spatial relationship with the position of the tracked hand-held device 24. The predetermined spatial relationship may be based on at least one of an orientation of the tracked hand-held surgical device 24, an operating mode of the hand-held surgical device 24, and profile data associated with the operator. The profile data may include the height of the operator 22. The predetermined spatial relationship may comprise adding a spatial offset (e.g., in the form of a vector having a certain length, such as 40 cm to 80 cm) to the position of the surgical device 24 that translates the position of the surgical device 24 towards the head (i.e., mouth) of the operator 22. The spatial offset reduces a distance between the focus position and the mouth of the operator 22, which improves constructive interference of sound signals that (potentially) include voice commands of the operator 22. Of course, any utterance of the operator 22 will still have to be checked as to whether or not it actually includes a voice command.

Beamforming the reception of the microphone array 14 towards the operator 22 also causes sound signals that do not originate from the operator 22 to interfere at least partially destructively, which reduces sound intensity of sound that does not originate from the operator 22.

Figure 11:
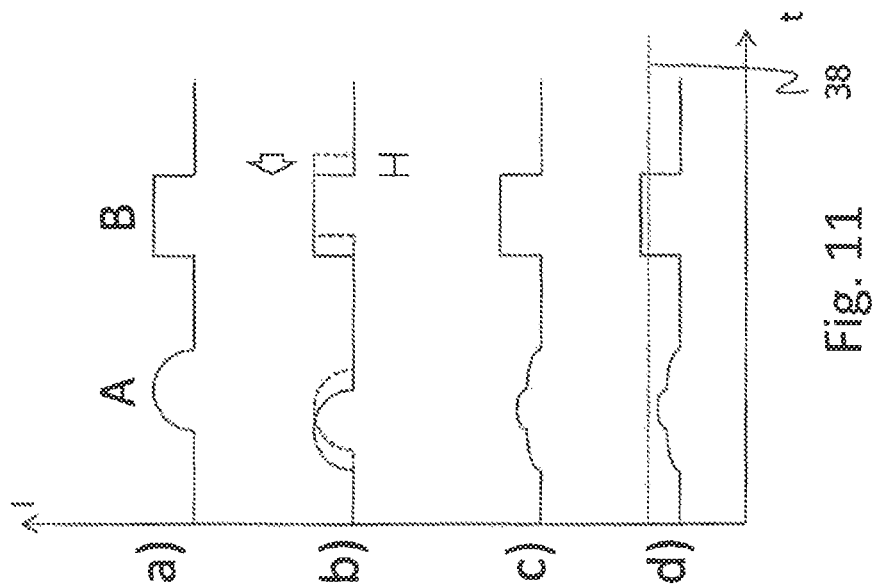
FIG. 11 shows sound signals containing voice commands, wherein beamforming is performed.
Figure 10:
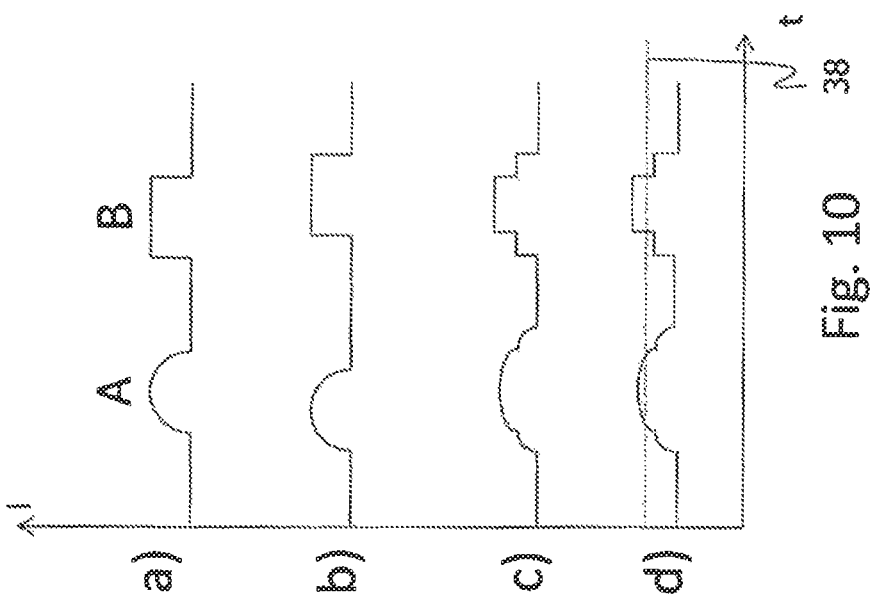
FIG. 10 shows sound signals containing voice commands, wherein no beamforming is performed.

FIGS. 10 and 11 show the effect of beamforming on a superposition of sound signals, wherein the sound signals contain potential voice commands A, B (i.e., utterances that will still have to be validated as voice commands based on their contents) issued by the non-operator 32 (issuing circular voice command A) and the operator 22 (issuing rectangular voice command B). Without limitation, it will in the following be assumed that the respective utterance actually includes a voice command A and B for control of a surgical system. FIG. 10 shows sound signals containing voice commands, wherein no beamforming is performed. FIG. 11 shows sound signals containing voice commands, wherein beamforming is performed.

More specifically, labels a) and b) of FIG. 10 show sound signals of two microphones 15 (such as microphones 15A, 15B shown in FIG. 3). Since no beamforming is performed, the voice commands A, B are randomly offset in time relative to each other.

Labels a) and b) of FIG. 11 show the same sound signals after being shifted temporally as part of the process of beamforming. Since the reception of the microphone array 14 is focused towards the operator 22, the voice commands B in both sound signals are temporally aligned.

Label c) of each of FIGS. 10 and 11 show the superposed sound signal generated from the corresponding sound signals of a) and b). Without beamforming, both commands A and B interfere randomly in the superposed sound signal, which results in approximately even sound intensity for both commands A and B. However, when beamforming is performed, in the superimposed sound signal the sound signals for command B interfere constructively, wherein the command A interferes randomly. Consequently, the sound intensity of command B is larger than the sound intensity of command A. (Another advantage of this approach is that the constructive interference may result in an improved signal-to-noise-ratio of command B.)

The difference of at least one of sound intensity and signal-to-noise-ratio may be used to distinguish command B uttered from the position of non-operator 32 from command A uttered from the position of operator 22. A command may be identified as being issued by the operator 22, when the sound intensity exceeds a predetermined threshold. Such a threshold 38 is shown in label d) of each of FIGS. 10 and 11. Without beamforming, the superposed sound signals of commands A and B both exceed the threshold 38, which does not allow determining which command was issued by the operator 22. With beamforming on the other hand, the superimposed sound signal of command A exhibits more destructive interference, preventing the sound signal to exceed the threshold 38. On the other hand, the superimposed sound signal of command B is based on constructive interference, so that its intensity exceeds the threshold 38. The command B can therefore be validated as a command that has actually been issued by the operator 22. The controller 10 is therefore able to improve the intelligibility of commands via beamforming and further allows identifying commands issued by the operator 22.

As explained above, the controller 10 is configured to perform sound processing which may comprise one or more of beamforming and determining that the voice command originates from an operator of the hand-held surgical device 24 based on a comparison condition. Independently from any of these two approaches, the controller 10 may be configured to implement further approaches.

For example, the controller 10 may be configured to generate a cancellation signal for at least one sound signal, wherein the cancellation signal is indicative of an interference signal contained in the sound signal. Such a controller 10 is further configured to at least partially cancel the interfering signal from the at least one sound signal using the cancellation signal. The interference signal may be any sound emitted in the operation environment that is not part of a command issued by the operator 22. The interference signal may be noise generated by the surgical device 24, a cooling fan, a fluorescent lamp, running water, and another device used during the surgical procedure.

The controller 10 may be configured to generate a cancellation signal that is identical or at least similar to the interference signal. The controller may be configured to cancel the interference signal by subtracting the cancellation signal from at least one of the sound signals of the microphones. The cancellation signal may comprise a pre-recorded sound signal. The cancellation signal may be generated based on at least one parameter of a set of parameters. The controller 10 may be configured to receive data indicative of the at least one parameters of the set of parameters. The operating set of parameters may comprise at least one of the instrument type, operating frequency, operating intensity, and operating mode of the surgical device 24.

Labels a) through c) of FIG. 12 shows sound signals 40, 42, 44 involved in cancelling an interference signal in a sound signal 40 from a microphone 15. Label a) of FIG. 12 shows a sound signal 40 of a microphone 15 generated from a voice command while the surgical device 24 is being operated. The surgical device 24 may, for example, be a power drill or a power saw. Such surgical devices 24 emit sound particularly at a variable or fixed operating frequency.

During operation of the surgical device 24, one or more parameters of the surgical device 24 are received by the controller 10 (e.g., drill type and operating frequency). The controller 10 is configured to generate a cancellation signal 42 based on the one or more operating parameters, as shown in label b) of FIG. 10. The cancellation signal 42 may comprise a superposition of sinus waves and/or pre-recorded sound signals.

The controller 10 is configured to at least partially cancel the interfering signal from the sound signal using the cancellation signal 42. By cancelling the interfering signal from the sound signal 40, the controller 10 generates a noise cancelled signal 44, in which the interference signal is at least partly removed. As a consequence, any voice command in the noise cancelled signal 44 has a lower chance of being misinterpreted, which improves safety and efficiency of the surgical procedure.

FIG. 12 shows the process of cancelling an interfering signal 42 from a single sound signal 40. The controller 10 may also be configured to cancel the interfering signal 42 from more than one sound signal. The controller 10 may be configured to cancel the interfering signal 42 from all sound signals of, for example, microphone array 14. Alternatively, the controller 10 may be configured to cancel the interference signal 42 from a superimposed sound signal generated from a plurality of such sound signals. The superimposed sound signal may be generated using beamforming, as explained above.

Processing sound signals as described herein requires a position signal that is related to the operator 22 (typically the surgeon) issuing the command. In order to obtain such a position signal, the operator 22 would commonly be required to wear a location device that allows obtaining a position signal. However, the sound processing described herein specifically uses a position signal obtained from the tracking system 12. The position signal is therefore used in two different applications: tracking the surgical instrument 24 and processing the sound signals. Since the sound processing described herein uses a position signal that would be determined by the tracking system 12 anyway, it is not necessary to provide any additional location device in regard to the operator 22.

As said, the controller 10 is configured to receive signals from the tracking system 12 and the plurality of microphones 15. The tracking system 12 and the plurality of microphones 15 operate based on spatial data (e.g., beamforming and tracking), which requires some form of coordinates and, sometimes, coordinate transformations. Such transformations, in turn, may require registrations, or calibrations, between dedicated coordinate systems. For example, the tracking system 12 may be associated with a first coordinate system and the plurality of microphones 15 may be associated with a second coordinate system.

The tracking system 12 and the plurality of microphones 15 may have a common coordinate system, meaning that the first and second coordinate systems coincide. To this end, the tracking system 12 and the plurality of microphones 15 may, for example be integrated within a single unit, wherein the tracking system 12 and the plurality of microphones 15 have a fixed spatial relationship relative to each other. In such a case, a coordinate calibration may be performed during manufacturing of the surgical system 1.

Alternatively, the tracking system 12 and the plurality of microphones 15 may be provided separately, for example in order to allow customizing the positions of the tracking system 12 and the plurality of microphones 15. As a result, the first and second coordinate system may not coincide. In such a case, the controller 10 may therefore be configured to perform a registration, or calibration, wherein a spatial relationship, or transformation, between the first and second coordinates is determined. To this end, a calibration device is required which is detectable by both, the tracking system 12 and the plurality of microphones 15.

Figure 13A:
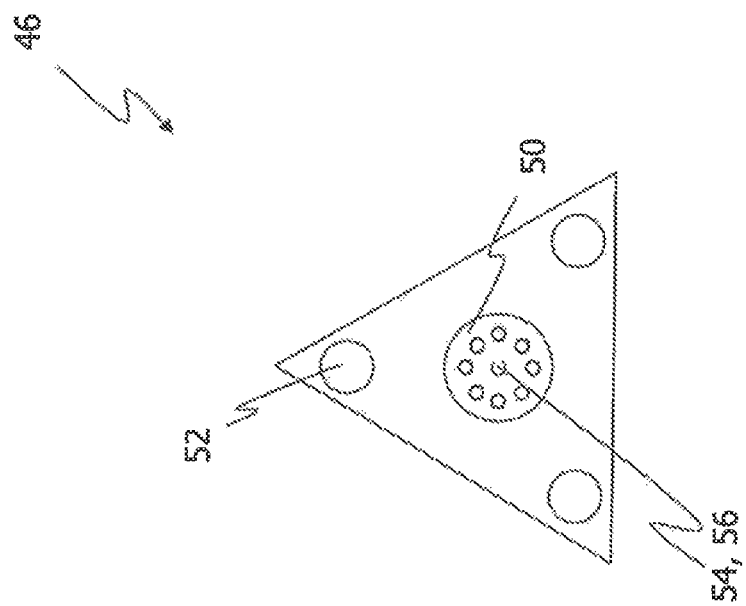
FIG. 13a shows a perspective view of a first embodiment of a calibration device.

FIG. 13A shows a perspective view of a first embodiment of a calibration device 46. The calibration device 46 comprises a tracker 48 trackable by the tracking system 12 and a speaker 50 configured to emit sound detectable by the plurality of microphones 15.

The tracker 48 shown in FIG. 13A comprises three optical tracking elements 52. The optical tracking elements 52 may be configured to reflect or emit light detectable by the tracking system 12. However, the tracker 48 may comprise any other type, number and form of tracking elements 52 suitable for tracking as described above for the device tracker 26. In an electromagnetic tracking system, for example, the tracker may comprise one, two or more tracking elements in the form of coils.

The speaker 50 may be configured to be controlled manually, e.g., by a switch, and/or remotely by the controller 10, e.g., via a wireless connection or an electrical line. In case the tracker 48 is an active tracker with electrically powered light sources, the tracker 48 may also be configured to be controlled manually or, alternatively, remotely by the controller 10.

The tracker 48 has a tracking centre 54 and the speaker 50 has a tracking centre 56. The tracker centres 54, 56 are points in space that may be used to define positions of the tracker 48 and the speaker 50 in any coordinate system. The tracking centres 54, 56 shown in FIG. 13A are spaced apart. In such a case, a first spatial relationship between the tracker 48 and the speaker 50 includes a (mathematical) translation 58 that needs to be taken into account during a calibration procedure.

Figure 13B:
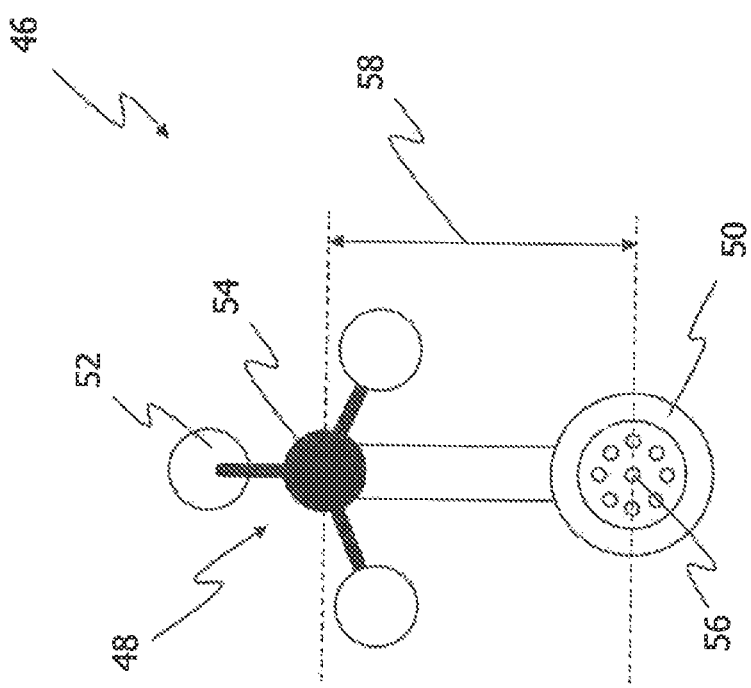
FIG. 13b shows a perspective view of a second embodiment of the calibration device.

FIG. 13B shows a perspective view of a second embodiment of the calibration device 46 with a tracker 48 and a speaker 50. The tracker 48 comprises three tracking elements 52 in form of light sources, but may comprise any other number and form of tracking elements 52 suitable for tracking as described above for the device tracker 26. The first and second embodiments of the calibration device 46 essentially differ from the first embodiment insofar as the tracking centres 54, 56 of the tracker 48 and the speaker 50 coincide. Therefore, the first spatial relationship between the tracker 48 and the speaker 50 does not include a translation that needs to be taken into account during a calibration procedure.

Figure 14:
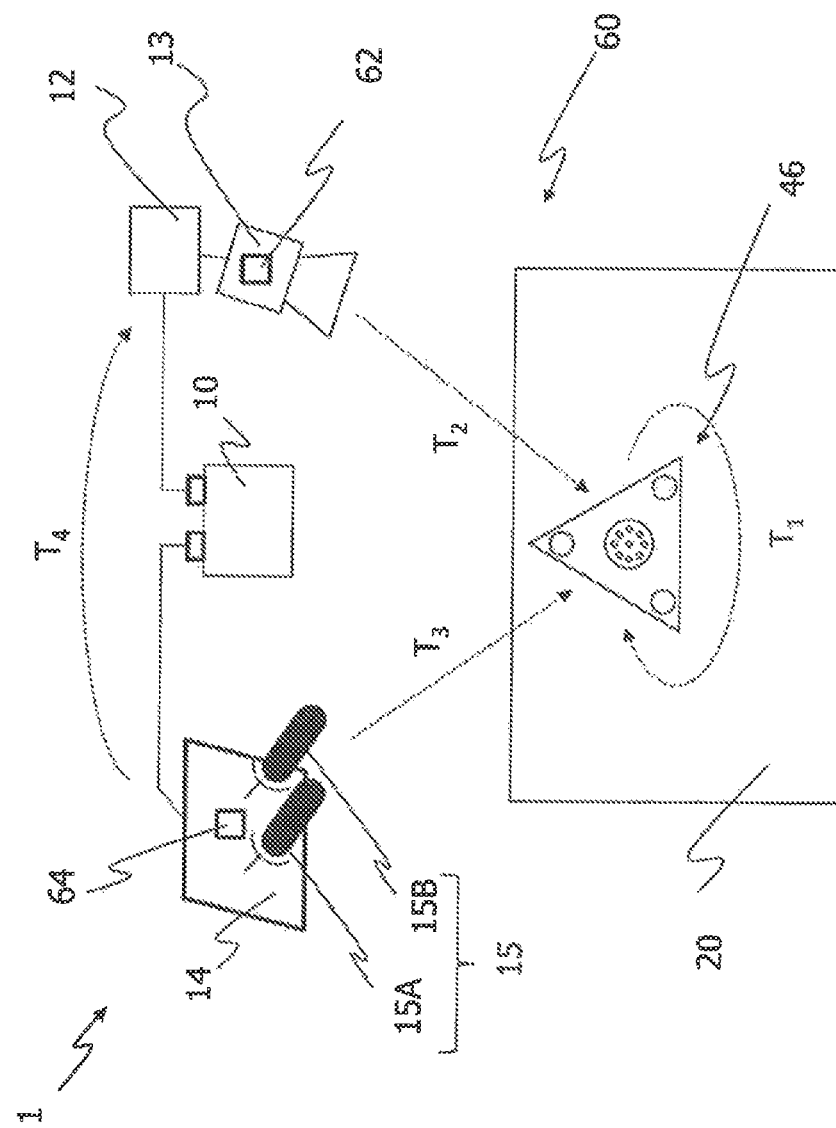
FIG. 14 shows a perspective view of a second embodiment of a surgical system.

FIG. 14 shows a perspective view of a second embodiment of a surgical system 1. The second embodiment of the surgical system 1 differs from the first embodiment essentially in that the surgical system 1 comprises a controller system 60 instead of only a controller 10. The controller system 60 comprises a controller 10 as described herein and a calibration device 46 as described herein.

The tracking system 12 is associated with a first coordinate system 62. The plurality of microphones 15 is associated with a second coordinate system 64. For the tracking system 12 shown in FIG. 14, the first coordinate system 62 is, for example, arranged in a geometric centre of an image plane of the camera 13 of the tracking system 12. For the plurality of microphones 15 shown in FIG. 14, the second coordinate system 64 is, for example, placed in a geometric centre of the plurality of microphones 15. However, any other point in space stationarily related to the tracking system 12 and the plurality of microphones 15 may be selected for arranging either of the two coordinate systems 62, 64, respectively.

During calibration, or registration, spatial relationships between different elements of the surgical system 1 need to be defined. A mathematical approach for defining the spatial relationships is a transformation, such as a transformation matrix. In the following, the spatial relationships will be described as such transformations using the expression "T".

The controller 10 has access to a first spatial relationship of the tracker 48 relative to the speaker 50. For the calibration device 46 shown in FIG. 14, the tracking centres of the tracker 48 and the speaker 50 coincide. Therefore, the first spatial relationship may be described by a transformation $T_1$ that is defined by an identity matrix. When using a calibration device 46 in which the tracking centres 54, 56 do not coincide, a transformation $T_1$ may be defined that transforms one of the tracking centres 54, 56 onto the other tracking centre 56, 54. For example, for the calibration device 46 shown in FIG. 13A, the transformation $T_1$ may be defined by the mathematical translation 58 (i.e., a vector from the one of the tracking centres 54, 56 to the other tracking centre 56, 54). For the calibration procedure described below, the calibration device 46 may be placed at a random or a predetermined position inside the operation environment 20.

The controller 10 is configured to determine a second spatial relationship of the tracker 48 relative to the first coordinate system 62. The second spatial relationship may be defined as a transformation $T_2$ and may be obtained by determining a distance and orientation of the tracker 48 relative to the first coordinate system 62 based on known geometric properties of the tracker 48 and calculating the particular transformation $T_2$ that translates the tracking centre 54 of the tracker 48 onto the origin of the first coordinate system 62.

The controller 10 is configured to determine a third spatial relationship of the speaker 50 relative to the second coordinate system 64. The third spatial relationship may be defined by a transformation $T_3$ and may be obtained by determining a position of the speaker 50 relative to the second coordinate system 64 via acoustic locating techniques as described above (e.g., via trigger moments or shifting sound signals relative in time). Optionally, the orientation of the speaker 50 may be calculated based on the orientation of the tracker 48 determined by the tracking system 12. This calculation requires that the orientation of the speaker 50 relative to the tracker 48 is known.

The controller 10 is further configured to determine a fourth spatial relationship of the first coordinate system 62 relative to the second coordinate system 64 based on the first, second and third spatial relationships. The fourth spatial relationship may be defined by a transformation $T_4$.

As can be seen in FIG. 14, the transformations $T_1$, $T_2$, $T_3$, $T_4$ form a closed ring of transformations. Therefore, the transformation $T_4$ can be obtained from a linear combination of the transformations $T_1$, $T_2$, $T_3$ using the equation:

$$T_4 = T_2 + T_1 - T_3 \qquad \text{equation(4)}$$

It is noted that the algebraic signs for each transformation $T_1$, $T_2$, $T_3$, $T_4$ in equation (4) depend on a direction in which each of the transformations are $T_1$, $T_2$, $T_3$, $T_4$ are defined. The algebraic signs in equation (4) correspond to the transformations as defined in FIG. 14 and may change when defined differently.

The transformation $T_4$ (and its inverse transformation $T_4^{-1}$) can be used to calculate the coordinates of an object in one of the two coordinate systems 62, 64 by applying the transformation $T_4$ (or its inverse transformation $T_4^{-1}$) to the coordinates of the object in the other one of the two coordinate system 64, 62.

The sound signals are generated by the plurality of microphones 15, to which the second coordinate system 64 is assigned, whereas the position signal is generated by the tracking system 12, which to which the first coordinate system 62 is assigned. Using the transformation $T_4$ obtained from the above calibration process allows the controller 10 to process the sound signals dependent on the position signal.

The calibration procedure for determining the fourth spatial relationship may be performed once. Alternatively, the controller 10 may be configured to determine the second, third, and fourth spatial relationships for a plurality of positions of the calibration device 46. This may be realized by positioning the calibration device 46 at a random or predetermined position and instructing the controller 10 to perform the determination of the second, third, and fourth spatial relationships. The controller 10 may then instruct a user to reposition the calibration device 46, whereupon the second, third and fourth spatial relationships are determined again.

Alternatively, the controller 10 may be configured to continuously determine the second, third, and fourth spatial relationships while a user is moving the calibration device 46 in the operation environment 20.

The controller 10 may be configured to determine a final result for the fourth spatial relationship by averaging over multiple fourth spatial relationships obtained for the multiple positions of the calibration device 46.

The calibration device 46 shown in FIGS. 13A, 13B, 14 is a device that is provided separately from the surgical device 24 or the device tracker 26. Alternatively, the surgical device 24 or the device tracker 26 may comprise the speaker 50, which can be used in combination with the device tracker 26 as a calibration device 46. The speaker 50 may be attachable to the surgical device 24 and/or the device tracker 26. The speaker may be integrated in the surgical device 24 or the device tracker 26. Alternatively, the surgical device 24, the device tracker 26, and the speaker 50 may be integrally formed in a single unit.

The features described in relation to the exemplary embodiments shown in the drawings can be readily combined to result in different embodiments. It is apparent, therefore, that the present disclosure may be varied in many ways. Such variations are not to be regarded as a departure from the scope of the invention as defined by the claims appended hereto.

The invention claimed is:

1. A controller for a surgical system, the controller being configured to:
   receive a position signal from a tracking system, wherein the position signal is indicative of a position of a hand-held surgical device that is tracked by the tracking system inside an operation environment;
   receive sound signals from a plurality of microphones spaced apart from the position of the hand-held surgical device and directed toward the operation environment; and
   process the sound signals dependent on the position signal comprising:
      determine, based on the sound signals received from the plurality of microphones, a position of a voice source of a voice command included in each of the sound signals; and
      determine that the voice command originates from an operator of the hand-held surgical device based on a comparison condition that evaluates a relationship between the determined position of the voice source and the position signal from the tracking system.

2. The controller according to claim 1, the controller being further configured to shift, based on the position signal, the sound signals relative to each other in time and then superpose the shifted sound signals to generate a superposition signal in such a way that sound signals received from a focus position related to the position of the hand-held surgical device interfere constructively.

3. The controller according to claim 2, wherein the focus position has a predetermined spatial relationship with the position of the tracked hand-held surgical device.

4. The controller according claim 2, wherein the controller is further configured to determine that there exists a voice command originating from an operator of the hand-held surgical device if the superposition signal contains a voice command that satisfies at least one detection condition.

5. The controller according to claim 4, wherein the at least one detection condition is a threshold condition.

6. The controller according to claim 1, the controller being further configured to:
- determine for each of the sound signals a trigger moment, in which an intensity of a sound signal exceeds a predetermined trigger threshold; and
- determine the position of the voice source based on a time relationship between the trigger moments.

7. The controller according to claim 1, the controller being further configured to:
- shift the sound signals relative to each other in time so as to temporally align the sound signals with respect to the voice command included in each sound signal; and
- determine the position of the voice source based on the time shifts for the temporal alignment of the sound signals.

8. The controller according to claim 1, the controller being further configured to:
- generate a cancellation signal for at least one sound signal, wherein the cancellation signal is indicative of an interference signal contained in the sound signal; and
- at least partially cancel the interfering signal from the at least one sound signal using the cancellation signal.

9. The controller according to claim 8, the controller being further configured to generate the cancellation signal taking into account at least one parameter selected from a parameter set comprising a type of hand-held device and one or more operating parameters of the hand-held surgical device.

10. A surgical system comprising:
- a plurality of microphones; and
- a controller configured to:
  - receive a position signal from a tracking system, wherein the position signal is indicative of a position of a hand-held surgical device that is tracked by the tracking system inside an operation environment;
  - receive sound signals from the plurality of microphones spaced apart from the position of the hand-held surgical device and directed toward the operation environment; and
  - process the sound signals dependent on the position signal comprising:
    - determine, based on the sound signals received from the plurality of microphones, a position of a voice source of a voice command included in each of the sound signals; and
    - determine that the voice command originates from an operator of the hand-held surgical device based on a comparison condition that evaluates a relationship between the determined position of the voice source and the position signal from the tracking system.

11. A method for operating a surgical system, the method comprising:
- receiving a position signal from a tracking system, wherein the position signal is indicative of a position of a hand-held surgical device that is tracked by the tracking system inside an operation environment;
- receiving a sound signal from a plurality of microphones spaced apart from the position of the hand-held surgical device and directed towards the operation environment; and
- processing the sound signals dependent on the position signal comprising:
  - determine, based on the sound signals received from the plurality of microphones, a position of a voice source of a voice command included in each of the sound signals; and
  - determine that the voice command originates from an operator of the hand-held surgical device based on a comparison condition that evaluates a relationship between the determined position of the voice source and the position signal from the tracking system.

12. The method of claim 11, further comprising shifting, based on the position signal, the sound signals relative to each other in time and then superpose the shifted sound signals to generate a superposition signal in such a way that sound signals received from a focus position related to the position of the hand-held surgical device interfere constructively.

* * * * *